United States Patent [19]

Yamaguchi et al.

[11] Patent Number: 5,078,488
[45] Date of Patent: Jan. 7, 1992

[54] METHOD AND APPARATUS FOR DETERMINING REFRACTIVE INDEX DISTRIBUTION

[75] Inventors: Ichirou Yamaguchi, Wako; Tadakatsu Shimada, Fukaya; Kazuo Koya, Gunma; Toshiyuki Suzuki, Yokohama, all of Japan

[73] Assignees: Rikagaku Kenkyusho, Saitama; Shin-Etsu Chemical Co., Ltd., Tokyo, both of Japan

[21] Appl. No.: 509,909

[22] Filed: Apr. 16, 1990

[30] Foreign Application Priority Data

Apr. 17, 1989 [JP] Japan ................... 1-97055
Apr. 17, 1989 [JP] Japan ................... 1-97056

[51] Int. Cl.$^5$ .............................. G01N 21/41
[52] U.S. Cl. ................... 356/73.1; 356/128
[58] Field of Search ................... 356/73.1, 128

[56] References Cited

U.S. PATENT DOCUMENTS 4,441,811  4/1984  Melezoglu et al. ............ 356/128

FOREIGN PATENT DOCUMENTS 1193880  9/1985  Canada ................... 356/128
0174708  3/1986  European Pat. Off. .
8102634  9/1981  World Int. Prop. O. .

OTHER PUBLICATIONS

Ito et al., "Automatic Measurement of Fiber Parameters; Dimensional Nonuniformities and Refractive Index Profiles"; Rev. of the Electrical Communication Laboratories, vol. 26 #3-4 Mar.-Apr. 1978, pp. 518-525.

Proceedings of the IEEE, vol. 68, No. 10, 1980, pp. 1198-1203 IEEE, H. M. Presby et al.: "The Index-Profile Characterization of Fiber Preforms and Drawn Fibers".

IEEE Journal of Quantum Electronics, vol. QE-18, No. 10, 1982, pp. 1451-1465, IEEE, W. J. Stewart: "Optical Fiber and Preform Profiling Technology" pp. 1462-1463.

Primary Examiner—Vincent P. McGraw
Attorney, Agent, or Firm—McAulay Fisher Nissen Goldberg & Kiel

[57] ABSTRACT

Determination of refractive index distribution is utilized, including data of all the positions of diffraction images on a plane, from the incident ray dispersed by the cylindrical glass rod when the ray passes therethrough. A linear approximation thereof is performed; and the angle of the outgoing ray is calculated using the intersection of the approximate lineation and a plane through which the incident ray passes. Much data can be employed to calculated the angle of the outgoing ray. This substantially improves the accuracy of measurement of the angle of the outgoing ray and further this makes it possible to determine the angle even if no image of the outgoing ray is present on the plane throgh which the incident ray passes.

11 Claims, 8 Drawing Sheets

Refractive Index

METHOD AND APPARATUS FOR DETERMINING REFRACTIVE INDEX DISTRIBUTION

BACKGROUND OF THE INVENTION

1. Field of the Invention

The present invention relates to a method for determining refractive index distribution of, for instance, a cylindrical glass rod used as rod lenses or a preform for use in making optical fibers as well as an apparatus for determining such refractive index distribution.

2. Background Prior Art

The refractive index of cylindrical glass rod used as preforms (base materials) for making optical fibers or rod lenses per se varies radially is distributed as a square distribution along their radial direction while remaining unchanged in the axial direction. Optical fibers can be obtained by drawing such a cylindrical glass rod. Therefore, it is quite important to correctly determine the refractive index distribution of the preform prior to drawing it into optical fibers, so that products having high quality would be obtained.

The principle of the method for determining refractive index distribution of a cylindrical glass rod is explained below referring to FIG. 3. In FIG. 3, reference numeral 10 represents a cylindrical glass rod. The reference numeral 27 represents a screen to which ray "b" of light incident upon the cylindrical glass rod 10 is perpendicular. The x-coordinate and y-coordinate are defined as origin "c" which is a point projected onto screen 27 by rectilinearly propagating the incident ray "b". When the cylindrical glass rod 10 is placed as traced with 2-point chain line, incident ray "b" enters the center of the cylindrical glass rod 10 and then passes rectilinearly through as outgoing ray "$d_0$", which projects at origin "c" on screen 27. Then if the cylindrical glass rod 10 is displaced in parallel from the place traced with the 2-point chain line to a place traced by the continuous line, the incident ray "b" passes through the cylindrical glass rod 10 refracting under refractive index distribution thereof and emerges from the cylindrical glass rod 10 as outgoing ray "$d_1$", which projects at point Xc of x-coordinate on screen 27. The point Xc is the displacement coordinate by displacing distance "t" of the cylindrical glass rod 10, thus is represented as a function of "t" as in the following formula:

$$Xc = f(t)$$

Outgoing angle $\Phi$ (t) has the following relation:

$$\Phi(t) = \tan^{-1}(Xc/L) = \tan^{-1}\{f(t)/L\}$$

In this formula, "L" represents the length from the center of the cylindrical glass rod 10 to the screen 27. The outgoing $\Phi$ (t) thus can be determined from measuring results of the points Xc by the displacing distances "t" of the cylindrical glass rod 10.

Then the refractive index distribution n(r) of the cylindrical glass rod is calculated from the following formula, using the angle $\Phi$ (t) of outgoing ray thus obtained:

$$n(r) = n_2 \left( 1 - \frac{1}{\pi} \int_r^a \Phi(t) \frac{dt}{(t^2 - r^2)^{\frac{1}{2}}} \right)$$

In this formula, "$n_2$" represents the refractive index of the surrounding area of the cylindrical glass rod 10 and "a" is the radius of the cylindrical glass rod 10.

Japanese Patent Provisional Publication Nos. 63-95336 and 63-95337 disclose methods for determining refractive index distribution of a cylindrical glass rod by using the above explained principle.

In the case where a cylindrical glass rod is prepared by, for instance, growing glass along its axial direction according to the VAD (Vapor-phase Axial Deposition) technique, layer structure may be formed within the growing glass and the layer structure often makes refractive index distribution of the resulting glass heterogeneous in the axial direction. Point "e(x,y)" in FIG. 3 shows a projected point of outgoing ray "$d_e$" on screen 27 from cylindrical glass rod 10 having striae deposited at the place traced with the continuous line. Incident ray "b" passes through the cylindrical glass rod 10 diffracting by the layer structure, the outgoing ray "$d_e$" disperses in the direction of the y-axis, and then is projected at the point "e(x,y)" far from the x-axis on the screen 27.

Conventionally, even if a cylindrical glass rod had layer structure and an outgoing ray was projected at a point "e" far from the x-axis, outgoing angle $\Phi$ was determined from only the x-coordinate of the point "e". Thus, it is difficult to correctly determine the angle $\Phi$ of the outgoing ray of the cylindrical glass rod having great deal of layer structure, the result being, that this causes determined values to be errors. If the refractive index distribution is calculated from such erroneous values of the angle $\Phi$ of the outgoing ray, the resulting refractive index distribution causes great variation in the portions of the cylindrical glass rod within which great deal of layer structure is present and thus a correct refractive index distribution cannot be obtained.

SUMMARY OF THE INVENTION

The inventors of this invention have conducted various studies for determining refractive, index distribution of the cylindrical glass rod and found that this determining process can effectively be improved by the following: All position data of the dispersed images of the outgoing ray obtained by making a ray of light incident upon a cylindrical glass rod from the direction perpendicular to the central axis of the glass are measured and calculated into approximate lineation, and then an angle $\Phi$ of the outgoing ray is determined by an intersection of the approximate lineation and a place through which the incident light passes. Thus, the present invention has been completed on the basis of this finding.

An object of the present invention is to provide a method for determining refractive index distribution which makes it possible to determine a correct refractive index distribution of a cylindrical glass rod used as, for instance, a preform for making optical fibers in which a great deal of layer structure may be present.

According to this object, one aspect of the present invention provides a method for determining refractive index distribution which comprises the following steps (a) to (g):

(a) making rays of light incident into the cylindrical glass rod from the direction perpendicular to the central axis of the cylindrical glass rod, (b) measuring position coordinates of diffraction images of "0" degree to "n" degree which are shaped by an outgoing ray transmitted through the cylindrical glass rod from said incident ray, (c) providing an approximate lineation from said position coordinates of the images, (d) calculating an intersection point of said approximate lineation and a plane which is perpendicular to the central axis of the cylindrical glass rod and through which the incident ray passes, (e) displacing in parallel the cylindrical glass rod to a radial direction thereof and to a perpendicular direction to the incident ray, (f) measuring the displacing distance of the cylindrical glass rod and (g) determining the refractive index distribution of the cylindrical glass rod from said intersection point in the step (d) and said displacing distance in the step (f).

Another object of the present invention is to provide an apparatus for determining a correct refractive index distribution of a cylindrical glass rod even if the rod has a great deal of layer structure therein.

According to this object, another aspect of the present invention provides an apparatus for determining refractive index distribution which comprises the following means (a) to (d):

(a) an optical system for minimizing spot areas of light rays from a light source at the center of the cylindrical glass rod and making the rays of light incident upon the cylindrical glass rod from the perpendicular direction to the central axis thereof, (b) means for displacing in parallel the cylindrical glass rod to a radial direction thereof and to a perpendicular direction to the incident ray, (c) means for an image pickup to observe images shaped by an outgoing ray from the cylindrical glass rod to transfer position coordinates and (d) means for calculating the refractive index distribution thereof from the displacing distances by said means for the displacing and said position coordinates.

A further object of the present invention, is to provide an improved apparatus for determining a correct refractive index distribution of a cylindrical glass rod.

According to this object, a further aspect of the present invention, is an apparatus for determining refractive index distribution of a cylindrical glass rod which comprises the following means (a) to (d):

(a) an optical system for minimizing spot areas of light rays from a light source at the center of the cylindrical glass rod and making the rays of light incident upon the cylindrical glass rod from the perpendicular direction to the central axis thereof, (b) means for displacing in parallel the cylindrical glass rod to a radial direction thereof and to a perpendicular direction to the incident ray, (c) means for an image pickup to observe images shaped by an outgoing ray from the cylindrical glass rod to transfer position coordinates and (d) means for calculating the refractive index distribution thereof from the displacing distances by said means for the displacing and said position coordinates: wherein said means for the image pickup is placed on a table which is movable to the direction of an optical axis of the means for the image pickup and said means for calculating the refractive index distribution containing: an arithmetic circuit for calculating an approximate lineation from said position coordinates; an arithmetic circuit for calculating a coordinate of an intersection point from said approximate lineation and a plane which is perpendicular to the central axis of the cylindrical glass rod and through which the incident ray passes; an arithmetic circuit for calculating for an angle of the outgoing ray from said coordinate of the intersection point and the displacing distance thereof by said means for displacing, and an arithmetic circuit for calculating the refractive index distribution of the cylindrical glass rod from said angle of the outgoing ray.

According to the method of the present invention in which the apparatus of this invention is utilized, data of all the positions of the images, which is formed, on a plane, from the incident ray dispersed by the cylindrical glass rod during the ray passing therethrough, are operated on to provide binary values to thus perform linear approximation thereof; and the angle of the outgoing ray is calculated using the intersection of the approximate lineation and a plane through which the incident ray passes. Therefore, much data can be employed to calculate the angle of the outgoing ray. This substantially improves accuracy of measurement of the angle of the outgoing ray and further this makes it possible to determine the angle even if no image of the outgoing ray is present on the plane through which the incident ray passes.

In the present invention, the cylindrical glass rod may be in the form of a coaxial cylindrical glass rod which can be used as a material for making optical fibers composed of a core portion and one or more clad portions.

BRIEF EXPLANATION OF THE DRAWINGS

The method and apparatus according to the present invention will be more apparent from the following detailed description described below with reference to the attached drawings, wherein.

DESCRIPTION OF THE PREFERRED EMBODIMENTS

The present invention will now be explained in more detail with reference to non-limitative specific embodiments.

Figure 1:
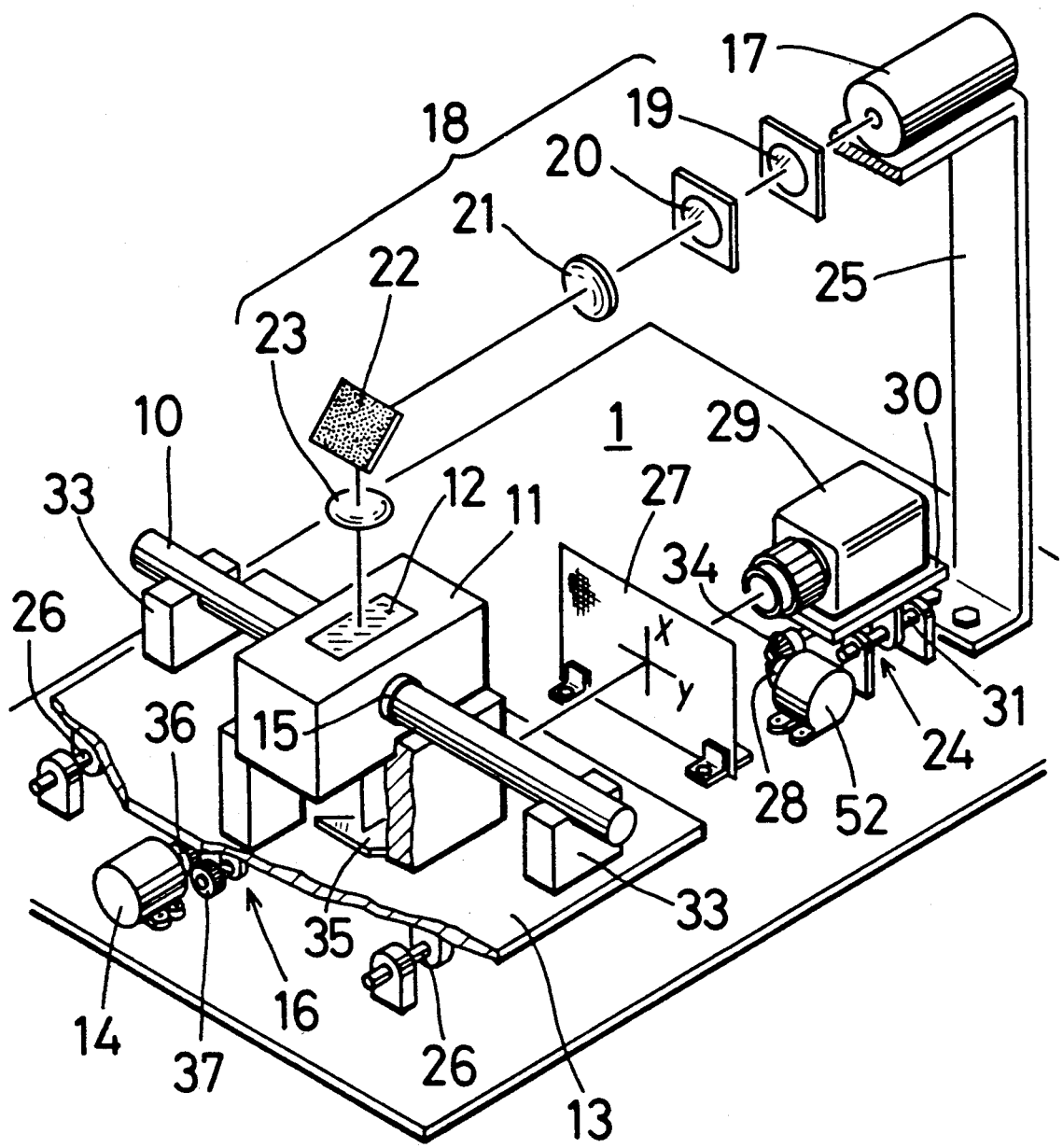
FIG. 1 is a perspective view of an embodiment of the apparatus according to the present invention.

FIG. 1 shows a schematic construction of an embodiment of the apparatus according to the present invention and in a partial cutaway view.

This apparatus is constructed on chassis 1. In FIG. 1, the reference numeral 10 represents a cylindrical glass rod to determine refractive index distribution which is used for a preform of optical fibers. The reference numeral 11 represents a cell which has transparent windows. The cylindrical glass rod 10 is fitted into cell 11 slidably through O-rings 15 and is supported on supporters 33 on a movable table 13. The cell 11 is filled with a matching oil 12 in order to prevent abrupt change in the refractive index at the boundary of the cylindrical glass rod 10 and the air possibly present in the cell 11.

Screw driving system 16 is mounted to an under part of the movable table 13 and is connected to pulse motor 14 by gears 36 and 37. The reference 26 represent driving guide shafts. When the pulse motor 14 rotates, the cylindrical glass rod thus moves to the radial direction thereof.

The reference 17 represents a light source such as He-Ne laser oscillator which is supported by supporter 25 on the chassis 1. The reference numeral 18 represents an optical system for making a ray of light incident upon the cylindrical glass rod 10. The optical system 18 has polarizing plate 19, λ/4-plate 20, lens 21, mirror 22 and lens 23. The incident optical system serves to converge the incident ray emitted from the light source 17 so that the spot area thereof becomes minimum at the center of cylindrical glass rod 10. Tubes and holders of the optical system 18 are not shown in the figures, but each is supported on the chassis 1. The reference numeral 27 represents a screen for projecting images by outgoing rays which transmit through the cylindrical glass rod 10 from the incident optical system 18 and reflect on mirror 35.

Figure 3:
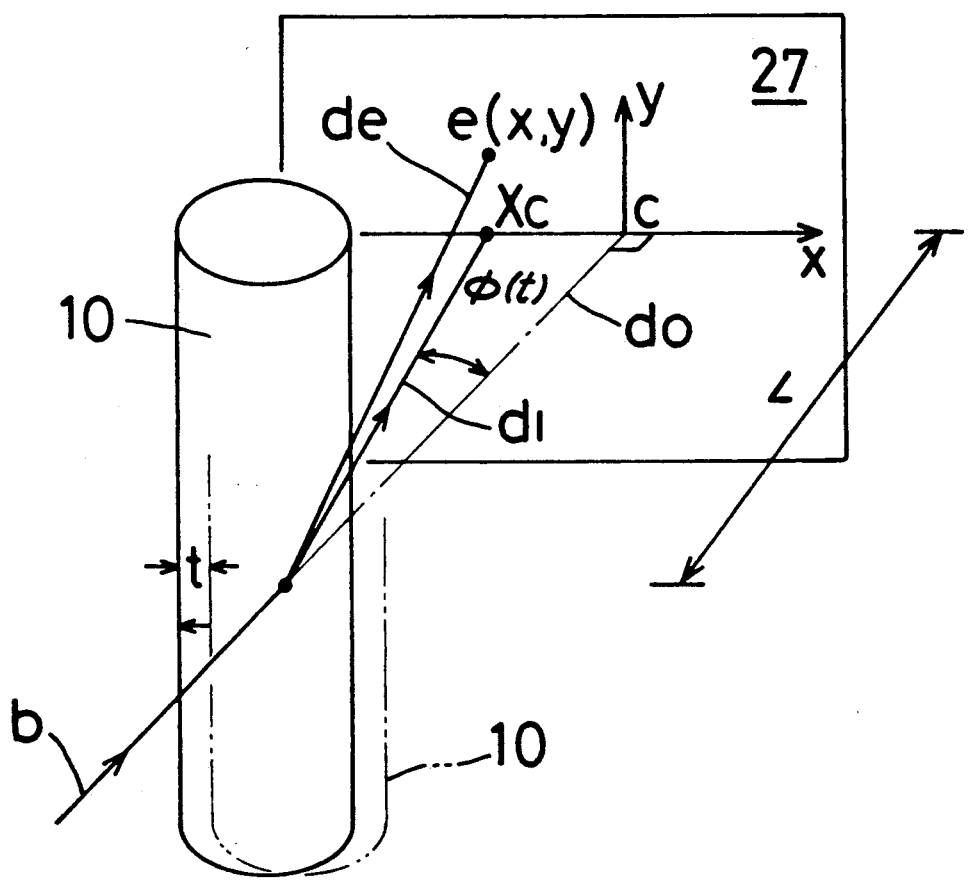
FIG. 3 is a diagram for explaining the principle for determining refractive index distribution.

As explained in FIG. 3, a y-axis is defined as the direction of the central axis of the cylindrical glass rod 10. In order to harmonize, the y-axis takes the axis of abscissa in the FIG. 1. When the cylindrical glass rod 10 has striae, as shown in FIG. 3, the "0" degree diffraction image is projected at an out point "e(x,y)" from the x-axis.

"0" degree to "n" degree diffraction images are projected on the screen 27 by outgoing rays from the cylindrical glass rod 10. The most intensive image of the project images is the "0" degree diffraction image and "1" degree, "2" degree, ... and "n" degree diffraction images have decreasing intensity, respectively.

In FIG. 1, the reference numeral 29 represents a video camera which observes projected images on the screen 27. The video camera 29 is placed on movable frame 30 which is driven by a screw driving system 24. The screw driving system 24 is connected to pulse motor 52 by bevel gears 34 and 28. The reference numeral 31 represents driving guide shafts. When the pulse motor 52 rotates, video camera 29 moves to the direction of the optical axis thereof.

Figure 2:
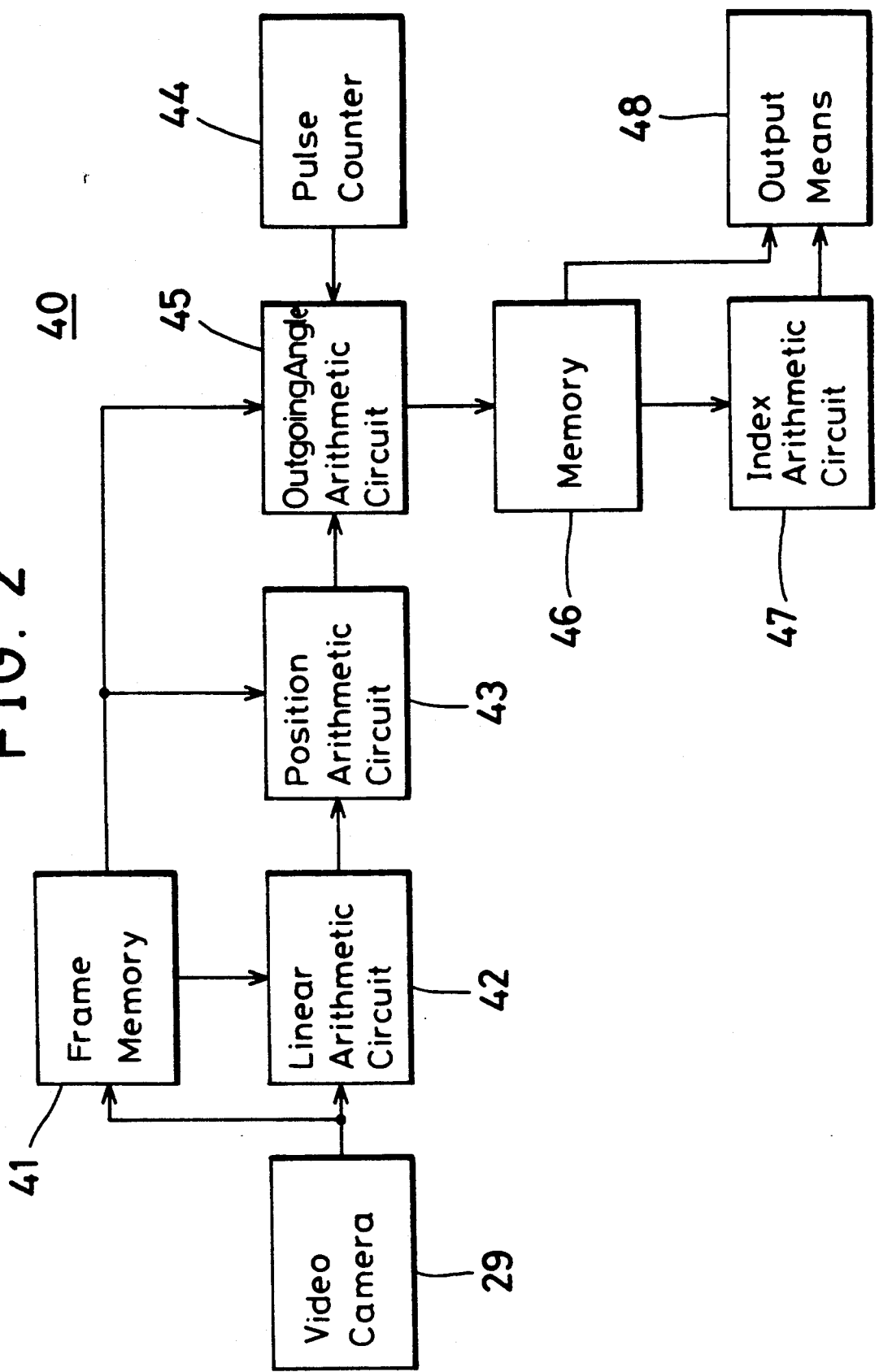
FIG. 2 is a block diagram showing a control portion of the foregoing embodiment of the apparatus shown in FIG. 1.

The video camera 29 connects to control portion 40 shown in FIG. 2. In the control portion 40 of FIG. 2, the reference numeral 41 represents a frame memory for storing data concerning to images on screen 27 which is observed by the video camera 29. The reference numeral 42 represents a linear arithmetic circuit for processing the stored data in the frame memory 41 to give binary values thereof and thus provides an approximate lineation by least square as expressed in the following formulae:

coordinate $(x_i, y_i)$, $i = 1$ to $m$ $$Sx = \sum_{i=1}^{m} x_i, Sy = \sum_{i=1}^{m} y_i, Sx^2 = \sum_{i=1}^{m} x_i^2,$$

$$Sy^2 = \sum_{i=1}^{m} y_i^2, Sxy = \sum_{i=1}^{m} x_i y_i$$

$$A = m \cdot Sxy - Sx \cdot Sy$$

$$B = Sy \cdot Sy - Sx \cdot Sx + m(Sx^2 - Sy^2)$$

$$C = Sx \cdot Sy - mSxy \quad D = B \cdot B - 4 \cdot A \cdot C$$

$$\alpha = \frac{-B + \sqrt{D}}{2A} \quad \beta = \frac{-B - \sqrt{D}}{2A}$$

$$a = \frac{Sy - bSx}{m} \quad b = \alpha \text{ or } \beta$$

Thus, an approximate lineation formula:

$$y = a + bx$$

can be obtained.

Figure 4:
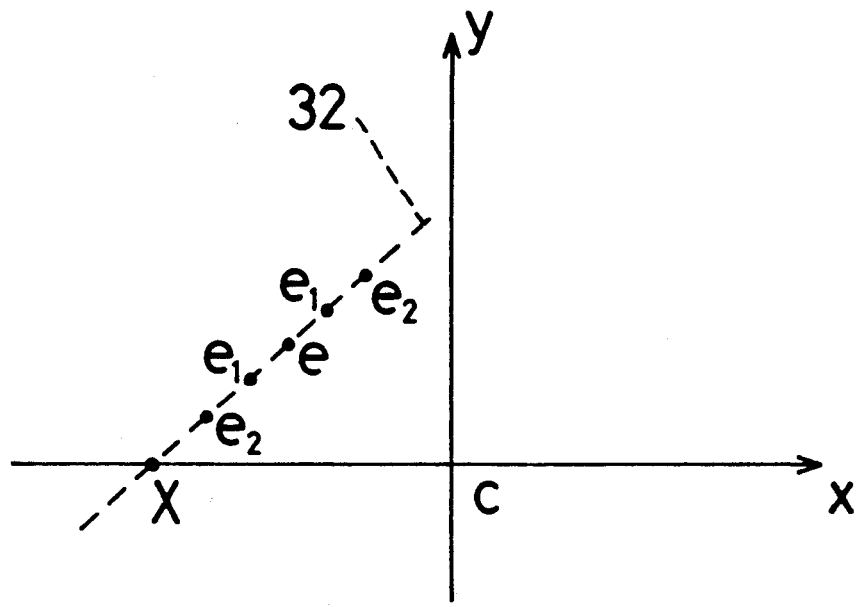
FIG. 4 is a diagram for explaining the functions of the embodiment shown in the preceding figures.

Concerning an example shown in FIG. 4, approximate lineation 32 can be obtained from "0" degree diffraction image "e", "1" degree diffraction images "$e_1$" and "2" degree diffraction images "$e_2$".

In FIG. 2, the reference numeral 43 represents a position arithmetic circuit for determining an intersection of the approximate lineation obtained by the linear arithmetic circuit 42 and a plane which is perpendicular to the central axis of the cylindrical glass rod 10 and through which the incident ray passes. Concerning the example shown in FIG. 4, an intersection X of the approximate lineation 32 and the x-axis is calculated.

In FIG. 2, the reference numeral 44 represents a pulse counter which counts pulses of displacing distance of the cylindrical glass rod 10 in the direction of the x-axis by rotating of pulse motor 14.

The reference numeral 45 represents an outgoing angle arithmetic circuit for calculating an outgoing angle $\Phi$ (t) from the intersection coordinate X and the displacing distance "t" by the following formula:

$$\Phi(t) = \tan^{-1}(X/L)$$

L is a distance from cylindrical glass rod 10 to screen 27 (See FIG. 3). The reference numeral 46 represents a memory which respectively stores the outgoing angle $\Phi$ (t). The reference numeral 47 represents an index arithmetic circuit for calculating the refractive index distribution of the cylindrical glass rod 10 on the basis of the outgoing angle $\Phi$ (t) of the following relation:

$$n(r) = n_2 \left\{ 1 - \frac{1}{\pi} \int_r^a \Phi(t) \frac{dt}{(t^2 - r^2)^{\frac{1}{2}}} \right\}$$

In this formula, "$n_2$" is a refractive index of matching oil 12 in cell 11; "r" is the radial parameter from the center of the cylindrical glass rod 10, and "a" is the radius of the cylindrical glass rod 10. The reference numeral 48 represents an output means for the outgoing angle $\Phi$ (t) and/or the refractive index distribution n(r)

of the cylindrical glass rod 10 comprising a display part and/or a recording part.

The refractive index distribution of the cylindrical glass rod 10 can be determined as followings:

The cylindrical glass rod 10 is set as shown in FIG. 1 and then the pulse motor 14 starts rotating to position the center of the cylindrical glass rod 10 to the optical axis of the optical system 18. In this positioning, an image projected on the screen 27 by a ray outgoing light transmitted through the cylindrical glass rod 10 is observed by the video camera 29 and then the signal of the image is transferred to the frame memory 41 to store therein. While displacing the cylindrical glass rod 10 to the x-axis (the radial direction thereof) by continuing to rotate the pulse motor 14, images of the outgoing ray on the screen 27 is observed by the video camera 29 and the image signal data are stored in the frame memory 41 in succession.

If the cylindrical glass rod 10 has a layer structure, the projected image positions "e", "$e_1$" and "$e_2$" (See FIG. 4) of the outgoing ray far from the x-axis. Then the approximate lineation 32 is obtained by the linear arithmetic circuit 42 from image data in the frame memory 41. The x-coordinate is calculated by the position arithmetic circuit 42 from the approximate lineation 32. The outgoing angle $\Phi$ (t) is calculated by the outgoing angle arithmetic circuit 45 from x-coordinate and distances "t" of displacing of the cylindrical glass rod 10 provided from the pulse counter 44 and then is stored in the memory 46. The outgoing angle $\Phi$ (t) is thus continuously stored in memory 46 while the distances "t" is changing by displacing of the cylindrical glass rod 10. The data of the outgoing $\Phi$ (t) is stored in memory 46 in succession. The stored data of the outgoing angle $\Phi$ (t) is displayed and/or printed out by the output means 48 while it is inputted to the index arithmetic circuit 47. The refractive index distribution n(r) is calculated by the index arithmetic circuit 47 from the data of the outgoing angle $\Phi$ (t) and then is displayed and/or printed out by the output means 48.

Figure 5:
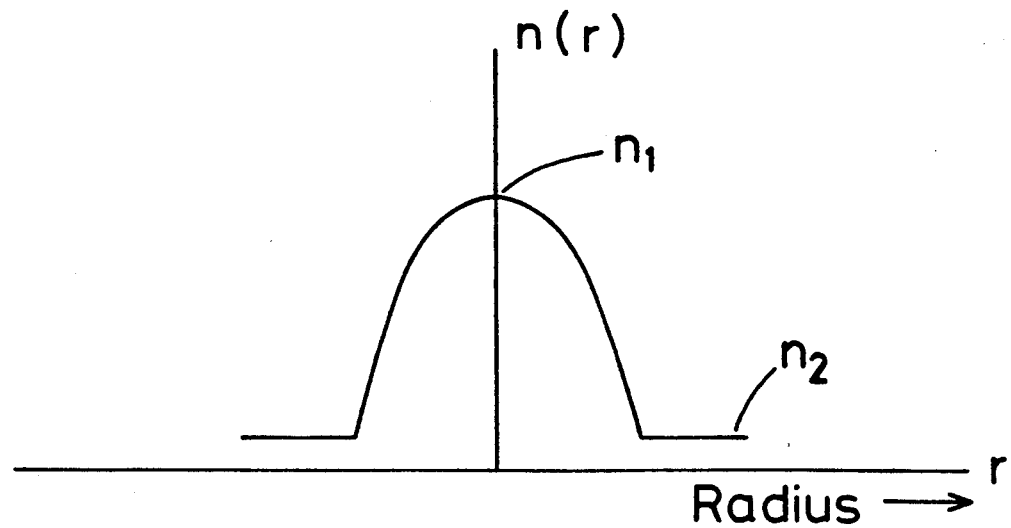
FIG. 5 is a diagram showing the refractive index distribution of a preform.
Figure 6:
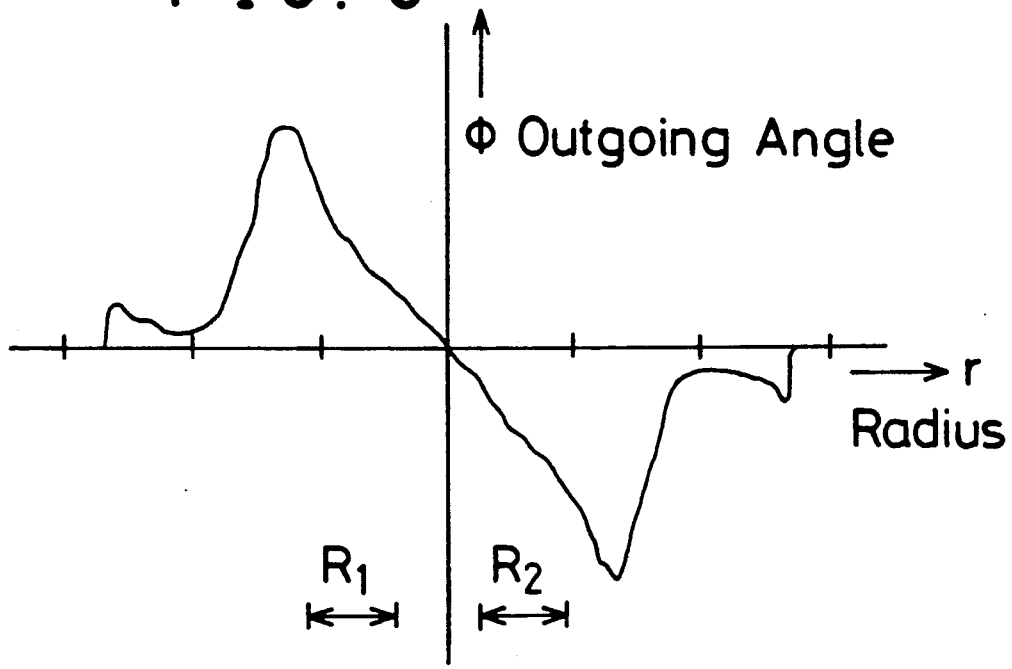
FIG. 6 shows the behavior of the angle of the outgoing ray determined according to the apparatus shown in the preceding figures.
Figure 7:
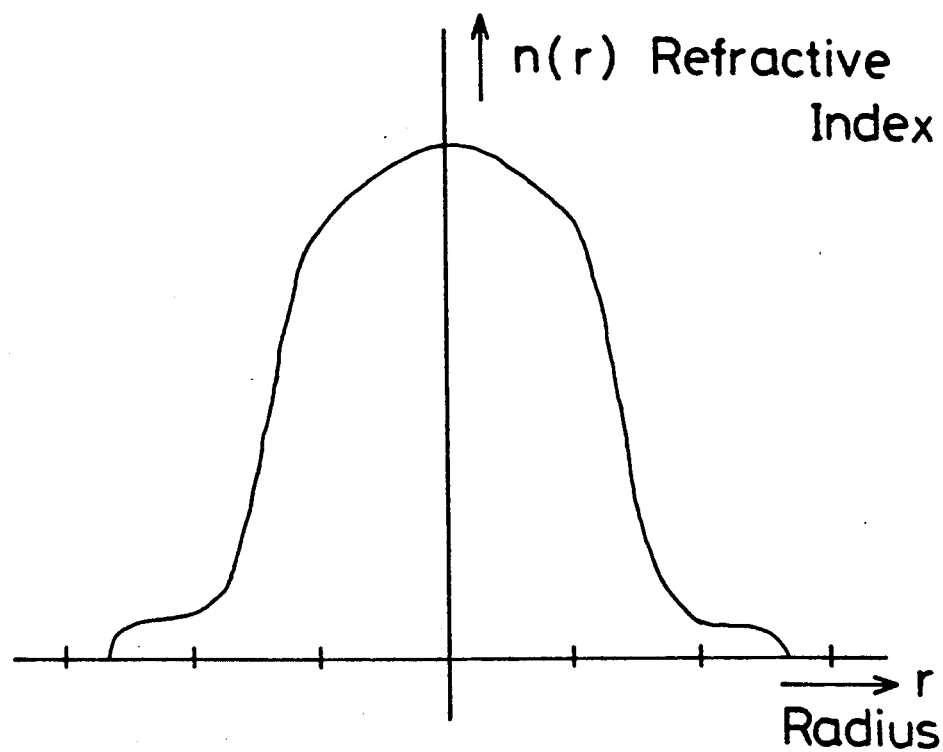
FIG. 7 shows the refractive index distribution calculated from the angle of the outgoing ray shown in FIG. 6.

According to the foregoing procedures, the relation was determined between the position at which a ray of light was made incident and the angle of the outgoing ray observed on a cylindrical glass rod 10 whose maximum refractive index of the core is "$n_1$" and the refractive index of the clad is "$n_2$" as shown in FIG. 5. The results thus obtained are shown in FIG. 6. There was not observed any marked variation in the angle $\Phi$ of the outgoing ray even if there were regions $R_1$ and $R_2$ of the cylindrical glass rod 10 in which a great deal of layer structure were present. The refractive index distribution n(r) was determined from these angles $\Phi$ of the outgoing ray and are found to be those shown in FIG. 7. This measurement was repeated 30 times to calculate a specific refractive index difference defined by the following relation:

$$\Delta = (n_1 - n_2) \times 100/n_1$$

Figure 8:
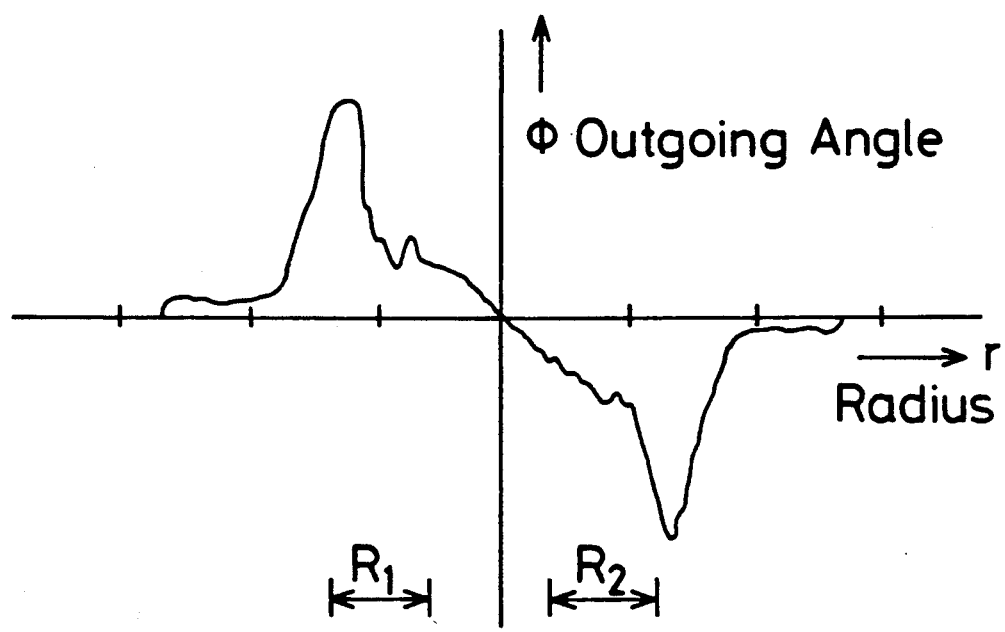
FIG. 8 is a diagram showing the characteristic properties of the angle of the outgoing ray obtained according to a reference example.
Figure 9:
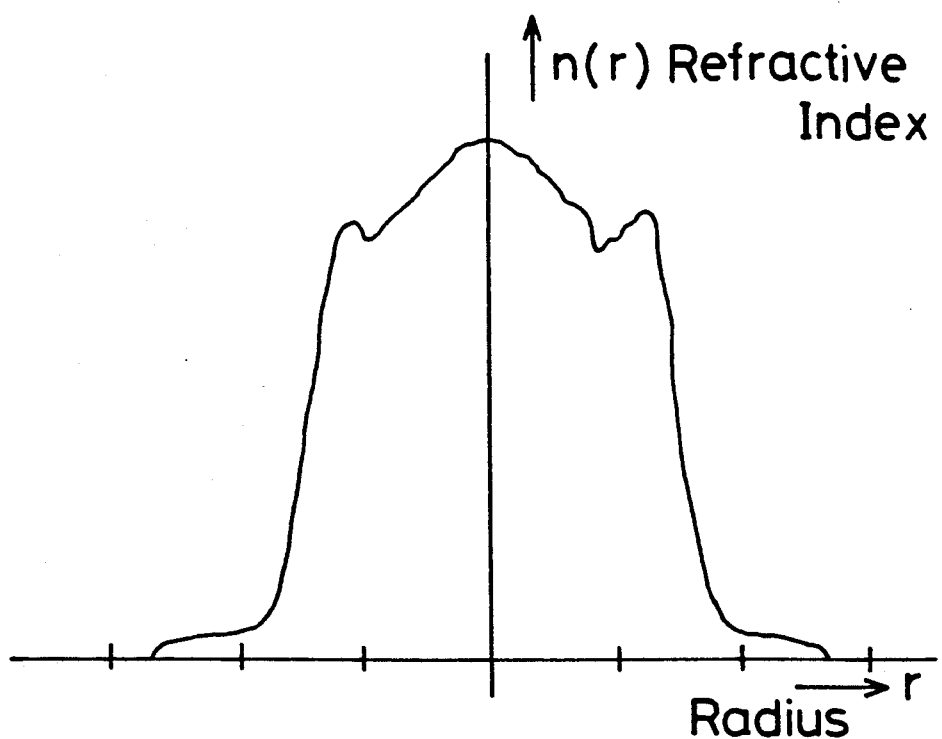
FIG. 9 is a diagram showing the refractive index distribution calculated from the angle of the outgoing ray shown in FIG. 8.

The standard deviation $\sigma$ of the specific refractive index difference $\Delta$ was calculated, and then was normalized with the specific refractive index difference $\Delta$ and thus the following relation was obtained: $(\sigma/\Delta) = 0.001$ In order to compare with the above explained example, an outgoing angle $\Phi$ was provided from a position of an incident ray and x-coordinate obtained by only use of "0" degree diffraction image "e(x,y)". This comparison was performed by using the same cylindrical glass rod 10, used in the above explained example, having layer structure. It was difficult to correctly determine the angle $\Phi$ of the outgoing ray at regions $R_1$ and $R_2$ having a great deal of layer structure as shown in FIG. 8, in the result, this caused determined value errors. Calculated from such erroneous values of the outgoing angle $\Phi$, the resulting refractive index distribution n(r) caused great variation at the portions of the cylindrical glass rod 10 within which great deal of layer structure were present as shown in FIG. 9.

Although the present invention has been described on the basis of the foregoing specific embodiments in which the projected images of the outgoing ray are observed by the screen 27 and the video camera 29, such observation can also be performed by using an image sensor and the same effect can be ensured.

Figure 10:
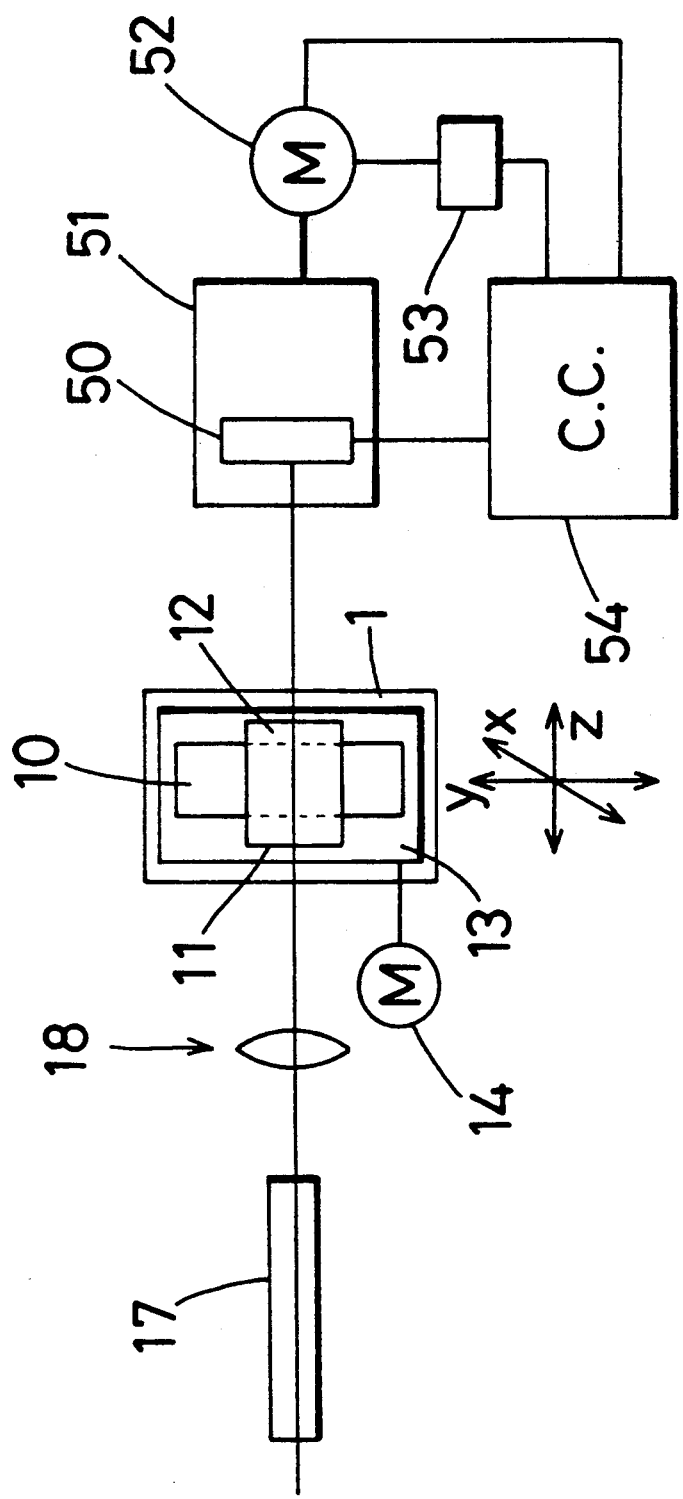
FIG. 10 is a schematic plane view of an other embodiment of the apparatus according to the present invention.

FIG. 10 is a schematic plan view of another embodiment than the above explained embodiment of the apparatus according to the present invention. In FIG. 10, the reference numeral 50 represents an image pickup tube, the reference numeral 51 represents a movable table on which the image pickup tube 50 is placed. Since the movable table 51 is driven by a pulse motor 52 to the direction of the optical axis of optical system 18, the image pickup tube 50 can be displaced to the same direction which means the direction of z-axis in FIG. 10. The reference numeral 53 represents a sensor for sensing the displacing distance of the image pickup tube 50 to the direction of z-axis. The reference numeral 54 represents a control circuit for controlling and calculating. FIG. 10 shows only principal portions which differ from that shown in FIG. 1, other details can be seen in FIG. 1.

Figure 11:
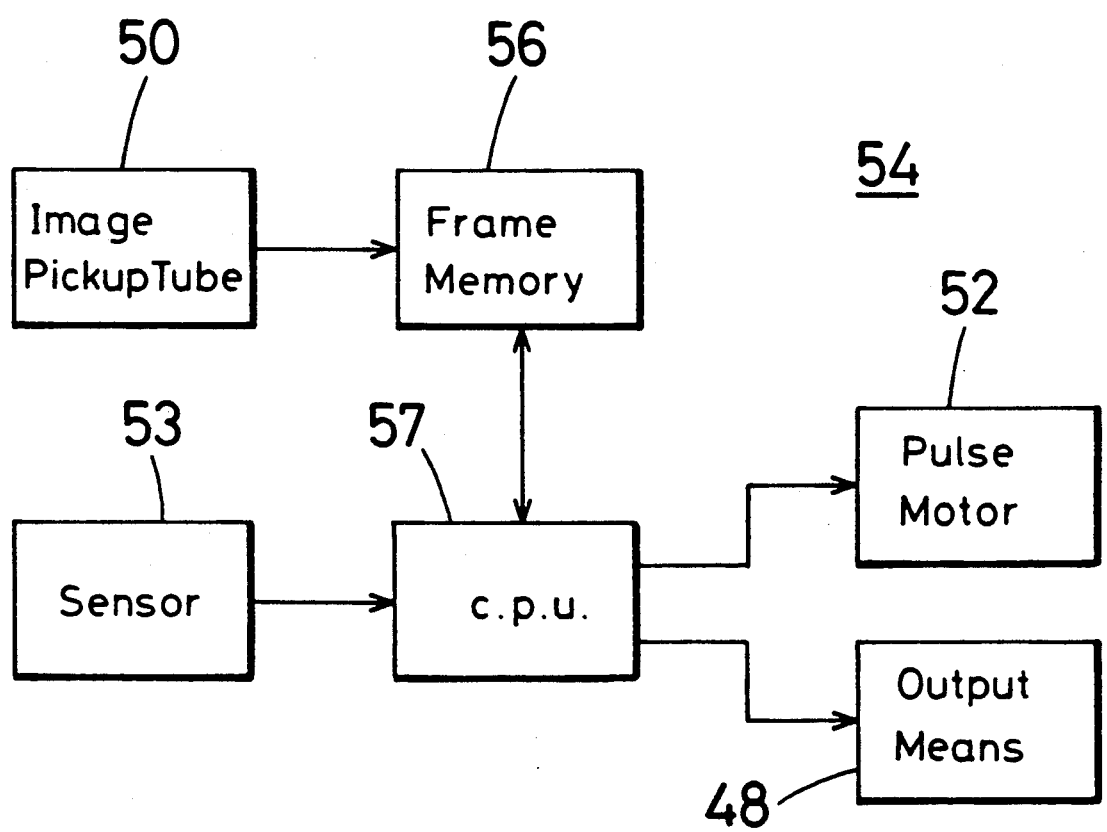
FIG. 11 is a block diagram showing a control portion of the foregoing embodiment of the apparatus shown in FIG. 10.

FIG. 11 shows a block diagram of control circuit 54 of the apparatus shown in FIG. 10. In FIG. 11, the reference numeral 56 represents a frame memory for storing the data from the image pickup tube 50. The reference numeral 57 represents a central processing unit for calculating outgoing angles $\Phi$ and refractive index distribution n(r) from the data in the frame memory 56 and then providing these data to output means 48. The central processing unit 57 also has the function of supplying a drive signal to the pulse motor 52 from the data in the frame memory. The output means 48 are the same devices as shown in FIG. 2.

The apparatus for determining refractive index distribution shown in FIGS. 10 and 11 operates as follows:

A ray of an incident light through an incident optical system 18 from light source 17 impinges on the cylindrical glass rod 10 from the perpendicular direction to the central axis thereof and refracts in inner parts thereof to emerge therefrom. This outgoing ray shapes an image and the image can be observed by the image pickup tube 50. Image data observed by the image pickup tube 50 are stored in the frame memory 56. The image data are transferred to the central processing unit 57 from the frame memory 56. Outgoing angles $\Phi$ and refractive index distribution n (r) are calculated from the image data in the central processing unit 57 and transferred to the output means 48. While the outgoing angle $\Phi$ is calculated, pulse motor 52 is driven by controlling of central processing unit 57 to displace the image pickup tube 50 on the movable table 51 so that the image pickup tube 50 can catch the images on the widest area thereof and does not cut off images on acceptable area thereof.

While the foregoing description and drawings represent the preferred embodiments of the present invention, it will be obvious to those skilled in the art that various changes and modifications may be made therein without departing from the true spirit and scope of the present invention.

What is claimed is:

1. A method for determining a refractive index distribution of a cylindrical glass rod, whose refractive index remains unchanged in its axial direction and varies along its radial direction, which comprises the following steps (a) to (g):
   (a) making rays of light incident on the cylindrical glass rod from a direction perpendicular to the central axis of the cylindrical glass rod,
   (b) measuring position coordinates of diffraction images of "0" degree to "n" degree which are shaped by an outgoing ray transmitted through the cylindrical glass rod from said incident ray,
   (c) providing an approximate lineation from said position coordinates of the images,
   (d) calculating an intersection point of said approximate lineation and a plane which is perpendicular to the central axis of the cylindrical glass rod and through which the incident ray passes,
   (e) displacing in parallel the cylindrical glass rod to a radial direction thereof and to a direction perpendicular to the incident ray,
   (f) measuring the displacing distance of the cylindrical glass rod and
   (g) determining the refractive index distribution of the cylindrical glass rod from said intersection point in the step (d) and said displacing distance in the step (f).

2. The method according to claim 1 comprising the following additional steps (h) and (i):
   (h) calculating an angle of the outgoing ray from said intersection point in the step (d) and said displacing distance in the step (f), and
   (i) determining the refractive index distribution of the cylindrical glass rod from the outgoing angle in step (h).

3. The method according to claim 1, wherein said intersection point of the approximate lineation in step (c) is provided by conversion of the position coordinates of the spots into binary values and the least square of the binary values.

4. An apparatus for determining a refractive index distribution of a cylindrical glass rod, whose refractive index remains unchanged in its axial direction and varies along its radial direction, which comprises:
   (a) optical system means for minimizing spot areas of light rays from a light source at the center of the cylindrical glass rod and for making the rays of light incident on the cylindrical glass rod from the direction perpendicular to the central axis thereof;
   (b) displacing means for displacing in parallel the cylindrical glass rod to a radial direction thereof and to a direction perpendicular to the incident ray;
   (c) imaging means for detecting projected spot images by rays of the light incident passing through from the cylindrical glass rod;
   (d) operating means for calculating an approximate lineation from the projected spot images;
   (e) position determining means for obtaining a position of intersection of the approximate lineation and a plane which is perpendicular to the central axis of the coaxial cylindrical glass and through which the incident ray passes; and
   (f) operating means for calculating the refractive index distribution of the cylindrical glass rod from the position of said intersection and a distance displaced by the displacing means.

5. The apparatus according to claim 4, wherein said displacing means is a driving device having a pulse motor.

6. The apparatus according to claim 4 further comprising a cell filled with a liquid having as a refractive index the same approximate refractive index of the outer surface of the cylindrical glass rod which is dipped in the cell.

7. The apparatus according to claim 4, further comprising a screen for having said spot images projected thereon and wherein said imaging means for detecting is a video camera.

8. The apparatus according to claim 4, wherein said imaging means is placed on a table which is movable to the direction of an optical axis of the imaging means.

9. The apparatus according to claim 4, wherein said operating means for calculating the refractive index distribution comprises an arithmetic circuit for calculating an angle of an outgoing ray from the position of the intersection and the displacing distance, and an arithmetic circuit for calculating the refractive index distribution of the cylindrical glass rod from the angle of the outgoing ray.

10. The apparatus according to claim 4 further comprising an output means for displaying the refractive index distribution of the cylindrical glass rod.

11. The apparatus according to claim 4 further comprising an output means for printing the refractive index distribution of the cylindrical glass rod.

* * * * *